(12) United States Patent
Bodlaender et al.

(10) Patent No.: US 8,323,191 B2
(45) Date of Patent: Dec. 4, 2012

(54) STRESSOR SENSOR AND STRESS MANAGEMENT SYSTEM

(75) Inventors: Maarten Peter Bodlaender, Eindhoven (NL); Ronaldus Maria Aarts, Eindhoven (NL); Privender Kaur Saini, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 1203 days.

(21) Appl. No.: 12/158,057

(22) PCT Filed: Dec. 19, 2006

(86) PCT No.: PCT/IB2006/054936
§ 371 (c)(1),
(2), (4) Date: Jun. 19, 2008

(87) PCT Pub. No.: WO2007/072412
PCT Pub. Date: Jun. 28, 2007

(65) Prior Publication Data
US 2009/0005657 A1      Jan. 1, 2009

(30) Foreign Application Priority Data
Dec. 23, 2005   (EP) ................................. 05112926

(51) Int. Cl.
*A61B 5/00* (2006.01)
*G06K 9/00* (2006.01)
*G06K 9/36* (2006.01)

(52) U.S. Cl. ........ 600/301; 128/922; 128/923; 382/110; 382/181; 382/232

(58) Field of Classification Search ........................ None
See application file for complete search history.

(56) References Cited

U.S. PATENT DOCUMENTS

| | | | | | |
|---|---|---|---|---|---|
| 5,343,871 | A | * | 9/1994 | Bittman et al. | 600/545 |
| 5,465,729 | A | * | 11/1995 | Bittman et al. | 600/545 |
| 5,794,187 | A | * | 8/1998 | Franklin et al. | 704/225 |
| 6,012,926 | A | * | 1/2000 | Hodges et al. | 434/236 |

(Continued)

FOREIGN PATENT DOCUMENTS

DE      19832361 A1      2/2000

(Continued)

OTHER PUBLICATIONS

Edge Detectiion: <http://en.wikipedia.org/wiki/Edge_detection> accessed on Apr. 8, 2012 (attached).*

(Continued)

*Primary Examiner* — Gregory A Morse
*Assistant Examiner* — Shirley Jian (57) ABSTRACT

A stressor detection system (100) comprises sensor means (101) arranged for being attached to a person for obtaining a time-varying signal representing a physical quantity relating to an environment of the person, and processing means (102) for deriving a stressor value from the obtained signal representing a degree to which the environment is inducing stress in the person. The processing means is arranged for deriving an amount of complexity comprised in the signal, and for deriving a higher stressor value for a larger amount of information. The processing means is further arranged for performing a spectral frequency analysis of the signal and for deriving the stressor value also in dependence on the spectral frequency analysis. The sensor means comprises a microphone (105), a camera (104), and a tri-axial accelerometer.

19 Claims, 1 Drawing Sheet

U.S. PATENT DOCUMENTS

| | | | |
|---|---|---|---|
| 6,198,394 | B1 | 3/2001 | Jacobsen et al. |
| 6,607,484 | B2 | 8/2003 | Suzuki et al. |
| 6,847,892 | B2 | 1/2005 | Zhou et al. |
| 6,894,610 | B2 | 5/2005 | Schubert et al. |
| 6,896,655 | B2 * | 5/2005 | Patton et al. ............ 600/300 |
| 6,925,425 | B2 | 8/2005 | Remboski et al. |
| 2002/0009119 | A1 | 1/2002 | Matthew et al. |
| 2005/0101872 | A1 | 5/2005 | Sattler et al. |
| 2006/0009702 | A1 * | 1/2006 | Iwaki et al. ............ 600/520 |

FOREIGN PATENT DOCUMENTS

| | | |
|---|---|---|
| JP | 10305016 A | 11/1998 |
| JP | 2005315802 A | 11/2005 |

OTHER PUBLICATIONS

J. Healey, et al: Quantifying Driver Stress; Developing a System for Collecting and Processing Bio-Metric Signals in Natural Situations, M.I.T Media Laboratory Computing Section Technical Report No. 483, Proceedings of the Rocky Mountian Bio-Engineering Symposium, Apr. 16-18, 1999, pp. 1-6.

C. M. Harris, HandBook of Acoustical Measurements and Noise Control, Reprint of 3rd Edition, Acoustical Society of America, pp. 23.1-23.7.

L. E. Kinsler, et al: Fundamentals of Acoustics 3rd Edition, John Wiley and Sons, New York, pp. 284-291.

B. G. Steele, et al: Quantifying Physical Activity on COPD Using a Triaxial Accelerometer, Chest, May 2000, vol. 117, pp. 139-1367.

F. Xiangsheng, et al: An Improved Integrated Electronic Nose for Online Measurement of VOCs in Indoor Air, Proc. IEEE Engineering in Medicine and Biology, 27th Annual Conf. Shanghai, China, Sep. 1-4, 2005, pp. 2894-2897.

* cited by examiner

STRESSOR SENSOR AND STRESS MANAGEMENT SYSTEM

FIELD OF THE INVENTION

The invention relates to a stressor detection system. The invention also relates to a method for detecting stressors.

BACKGROUND OF THE INVENTION

Many medical experts agree that stress is an important factor in disease prevention and recovery. Measuring vital body signs to calculate a measure of user stress is known, for example a way to measure the stress-level of a car driver, including a camera/observer recording the road condition, is described in "Quantifying driver stress: developing a system for collecting and processing bio-metric signals in natural situations," by Healey J, Seger J, Picard R., in: Biomed. Sci. Instrum. 1999; 35:193-8, referred to hereinafter as "Healey". It is also known that national and other legislation place boundaries on noise-levels and other external signals/influences to workers.

In U.S. Pat. No. 6,607,484, a behavior and stress management recognition apparatus is disclosed. It comprises a reference sensor information corpus storing records of environment (season, time, place, posture, action, behavior, and expected behavior), physical information (pulse rate, body temperature, galvanic skin reflex (GSR), and voice pitch), degree of stress, and dialogue structure. It further comprises storing subjective (stress) data for persons in the address book of personal information management (PIM) software. It further mentions an ultrasonic distance sensor for determining if a person enters someone's personal space, an odor sensor for determining a bad smell or strong smell, and determining the degree of stress from task data and schedule.

The existing system is relatively complex and requires a lot of user interaction to learn the stressfulness of any particular situation, which makes the stress measurement relatively subjective. It only takes into account a limited number of aspects of relevant environmental circumstances that may be stress inducing. The cited systems do not provide accurate information about the stressors in an environment of a person.

SUMMARY OF THE INVENTION

It is an object of the invention to provide a system for obtaining more accurate information about stressors in an environment of a person.

This object is realized by the first aspect of the invention, comprising
  sensor means arranged for being attached to a person for obtaining a time-varying signal representing a physical quantity relating to an environment of the person, and
  processing means for deriving a stressor value from the obtained signal representing a degree to which the environment is inducing stress in the person.

The obtained time-varying signal is especially suitable for applying further processing steps. A system with build-in knowledge about signal patterns or signal characteristics and their stress-inducing and/or stress-reducing properties can provide relatively accurate information about the stress induced on a person. Moreover, a degree to which a physical phenomenon is inducing and/or reducing stress can be quantified objectively using prior knowledge applicable in general and/or knowledge specific to the person or to a group that the person belongs to. Such specific and general knowledge may be obtained a priori and embedded in the system algorithmically and/or using a table lookup mechanism or database. Not only stressors can be determined, but also fear-inducing circumstances and fatiguing circumstances. Also relaxing circumstances can be determined and can be used to determine a relaxing value and to compensate the stressor value by decreasing the stressor value based on the relaxing value.

Preferably, the stressor value is normalized between 0 and 1 or between any predetermined upper and lower bound. Alternatively, predetermined fixed points may be used. In any way, it is preferred that the stressor value is normalized in such a way that it becomes possible to compare the stressor value established by different embodiments of the invention. For example, it should advantageously be possible to compare a stressor value obtained from a stressor detection system comprising a light sensor with a stressor value obtained from a stressor detection system comprising a microphone. This can be realized by normalizing the stressor value such that 0 corresponds to a relaxation-inducing environment that does not induce any stress, and 1 corresponds to an extremely stress-inducing environment, for example an environment known to cause permanent physical damage.

In an embodiment of the invention, the processing means is arranged for determining an amount of complexity comprised in the measured signal, and for deriving a higher stressor value for a larger amount of complexity.

The amount of complexity comprised in the measured signal can be determined by computing the amount of information in the signal or the entropy of the signal. Complex signals are correlated with a higher degree of induced stress, and therefore determining the amount of information comprised in the signal, or for example the Kolmogorov complexity can be used as an indicator relating to the stressor value, where advantageously a high complexity is related with a high amount of induced stress.

In an embodiment of the invention, the processing means is arranged for performing a spectral frequency analysis of the signal and for deriving the stressor value also in dependence on the spectral frequency analysis.

A spectral frequency analysis can also be used for determining the amount of stress induced. The spectral frequency analysis can be performed in many ways. For example, it can be used to estimate the complexity of the signal, which is related to the stressor value, because relatively complex signals typically comprise more frequency components than relatively straightforward signals. Also, certain frequency ranges may be more stress inducing than other frequency ranges. Some frequencies may not even be noticed by the person, whereas other frequencies may cause a relatively large amount of stress if the person is exposed to the signal with that frequency, in particular if the person is exposed to the signal with that frequency for a relatively long period of time. Advantageously the system recognizes a combination of frequencies that is related to stress. Also, the system can use for example time-frequency analysis to detect stress induced by signals with time-varying frequencies.

In an embodiment of the invention,
  the sensor means is arranged for obtaining a further time-varying signal representing a further physical quantity relating to an environment of the person,
  the processing means is arranged for deriving a further stressor value from the further obtained signal and for deriving a combined stressor value from the stressor value and the further stressor value.

Any number of signals and measurements can be obtained representing any number of physical quantities relating to an environment of the person and/or any number of physical or physiological quantities relating to the person. The processing means can derive the stressor value in dependence on these signals and measurements. For example, the processing means can establish stressor values corresponding to each of the respective signals and measurements, and establish a combined stressor value by combining the stressor values. The combining can be established by deriving a weighted sum of the stressor values. The combining can also be established by deriving a maximum of the stressor values. Preferably the stressor values are normalized before establishing the weighted sum or the weights are adjusted to perform the normalization and summation in one step. Also a mutual enforcement scheme may be used wherein simultaneous presence of different stressors results in a higher stressor value than a weighted average of the stressor values.

In an embodiment of the invention, the sensor means comprises a microphone and the obtained signal comprises an audio signal obtained from the microphone.

Sound, or audible signals, can be an important factor causing stress in the person. Especially audio signals that the person is able to hear may induce stress. Preferably the processing means is arranged for extracting a signal component comprising frequencies that the person is able to hear.

In an embodiment of the invention, the processing means is arranged for deriving the stressor value also in dependence on at least one of:
  an amplitude of the audio signal,
  an envelope of the audio signal,
  a dose of the audio signal, and
  a loudness of the signal.

In an embodiment of the invention, the processing means is arranged for giving a larger weight to a disturbing component of the audible signal component, the disturbing component comprising frequencies
  above a predetermined bound and below an upper bound of frequencies that the person is able to hear, where the predetermined bound is smaller than the upper bound, or
  frequencies below a predetermined bound and above a lower bound of frequencies that the person is able to hear, where the lower bound is smaller than the predetermined bound.

Sound frequencies that are relatively close to the limits of what the human ear can detect, can be especially stress inducing.

In an embodiment of the invention, the sensor means comprises a light sensor for obtaining a light intensity signal representing an intensity of visible environmental light, and the processing means is arranged for deriving the stressor value in dependence on the intensity.

Environmental light is another type of a potentially stress-inducing circumstance a person may be exposed to.

In an embodiment of the invention, the sensor means comprises a light sensor for obtaining a plurality of light signals each representing the intensity of a distinct color component of environmental light, and the processing means is arranged for deriving the stressor value in dependence on the light signals.

Different color compositions in environmental light, for example caused by different types of natural and/or artificial light sources or caused by a light filtering, may be a cause of stress in a person.

In an embodiment of the invention, the sensor means comprises a camera for obtaining at least one image relating to what the person is looking at, and the processing means is arranged for deriving the stressor value also in dependence on the image.

Not only the environmental light intensity and color are important stress-inducing factors, but also the contents of the image that the person sees is important. Advantageously, the processing means can be arranged for performing a pattern recognition of the image. The pattern recognition can be used for recognizing an object, where the object may be a person, a face, a tool, a wall, or any other object imaginable. Facial expressions may be recognized, for example faces with an angry or a happy facial expression can be distinguished as distinct types of objects with different stressor values. Also, gestures can be recognized such as a "middle finger" gesture, which is believed to cause stress. A gun being pointed to the person can be recognized. This is a combination of an object and a gesture that can be detected using for example image-processing techniques. A gun pointing to the person is believed to cause stress and fear. Also fear inducing objects or gestures can be detected to obtain a fear-inducement value. Preferably a storage means is arranged for storing patterns related to objects and/or gestures, each object or gesture being related to a stressor value. The stressor value may be predefined for each object or group or type of objects or gestures. The knowledge about stressor values may also be gathered during operation of the system automatically as set forth.

The camera can be arranged for obtaining a sequence of images relating to what the person is looking at, and the processing means is arranged for deriving the stressor value in dependence on the sequence of images. Processing a sequence of images can give a more reliable recognition of an object and thus can provide a more accurate estimate of the stressor value. In addition, time-dependent changes of objects can be tracked. Also, more complex gestures can be recognized. Objects moving towards and/or away from the person can be detected and related to the stressor value. For example, 'a face with an angry facial expression moving towards the person' can be associated with a higher stressor value than either 'a face with an angry facial expression' or 'a face moving towards the person' alone.

In an embodiment of the invention, the processing means is arranged for deriving an amount of complexity of the at least one image and for deriving the stressor value also in dependence on the amount of complexity of the at least one image.

Complex images require a relatively large amount of cognitive effort and can be stress-inducing.

In an embodiment of the invention, the processing means is arranged for deriving an amount of movement from the at least one image and for deriving the stressor value also in dependence on the amount of movement.

In an embodiment of the invention, the processing means is arranged for performing an object recognition on the at least one image and for deriving the stressor value also in dependence on the object recognition.

In an embodiment of the invention, the sensor comprises an acceleration sensor for obtaining an acceleration signal, and further comprising means for extracting from the acceleration signal an externally-induced acceleration signal representing an acceleration of the person not caused by a muscle contraction of the person, and the processing means is arranged for taking into account the externally-induced acceleration signal.

Acceleration, such as externally induced vibrations, can be a cause of stress. In particular vibrations with a high intensity are associated with a high stressor value. Also, repetitive vibration patterns can cause a high stressor value.

In an embodiment of the invention, the means for extracting is arranged for including an acceleration signal component with frequencies below a predefined lower threshold and further including an acceleration signal component with frequencies above a predefined upper threshold, where the upper threshold is larger than the lower threshold.

It is believed that accelerations of humans self-induced by human muscle contractions are mainly in the range of approximately 1 Hz to 15 Hz. Therefore, a relatively simple way to find the externally induced accelerations is to extract acceleration signal components having a frequency that is not in that range. The bounds of 1 Hz and 15 Hz are indicative only because, for example, relatively young, small, or light people may have quicker movements and therefore higher-frequency self-induced acceleration patterns than relatively old, large, or heavy people.

An embodiment of the invention further comprises an electromyography system for obtaining an electromyography signal and wherein the means for extracting is arranged for performing the extracting also in dependence on the electromyography signal.

Self-induced human accelerations may be detected because such a self-induced acceleration is often preceded by and/or often coincides with a muscle contraction within the person. By measuring electromyography signals related to muscle contractions, the muscle contractions can be measured, and it becomes possible to correlate measured acceleration with muscle contractions and remove acceleration components related to the muscle contractions from the signal, which results in an acceleration signal mainly consisting of externally-induced acceleration components.

An embodiment of the invention further comprises
 means for obtaining a stress value relating to stress experienced by the person, and
 means for establishing a relation between the signal and the stress experienced by the person.

These provisions allow for the system to learn automatically for improving the accuracy of the stressor value. The stressor value produced by the processing means can be compared to the obtained stress value, and if a difference is detected, a model internal to the processing means can be adjusted such that the model better reflects the relation between the signal and the stress experienced by the person. The model can be improved during operation of the system automatically, for example by correlating the obtained signal with a physiological measurement indicative of the stress of the person. The model can be implemented using for example an artificial intelligence method or a regression analysis. This model can be used to provide a stressor value with higher accuracy by taking into account idiosyncrasies.

In an embodiment of the invention, the means for obtaining the stress value is arranged for obtaining a physiological quantity of the person relating to stress experienced by the person.

The physiological quantity of the person can comprise for example at least one of pulse rate, body temperature, galvanic skin reflex (GSR), and voice pitch. These quantities are known to be relating to stress. Alternatively or in combination a user input via a user interface may be used indicative of the stress of the person.

An embodiment of the stressor detection method comprises deriving a stressor value from a time-varying signal, the time-varying signal representing a physical quantity relating to an environment of the person, the stressor value representing a degree to which the environment is inducing stress in the person

BRIEF DESCRIPTION OF THE DRAWINGS

These and other aspects of the method of the invention will be further elucidated and described with reference to the drawing, in which.

DETAILED DESCRIPTION OF THE INVENTION

In general it can be seen that there is a difference between stress and the signals that caused the stress, the stressors. We distinguish various types of stressors. First, sensory stressors can be loud and/or varying noise levels, light levels, acceleration and vibration, strong and varying smell all are observed by the human senses and are sources of stress. Especially intensity and (variation of) rhythms are significant. Second, symbolic stressors. For example, a soft noise can be a significant source of stress, if the observing human recognizes the symbolism in the noise. For example, pointing a gun at someone typically causes stress, as the person recognizes the object and knows that he is in mortal danger. Symbolic stressors can depend on the background and history of the human. Third, there is an undefined area between the first and second. Low-level symbolism such as for example yellow for danger and pink for safe, are easy to measure, but still are based on cognitive notions.

The system according to the invention allows in a simple and sensible way to monitor stressors and quantify the long-term stressor-level a consumer is exposed to. Therefore he or she is helped to judge whether an environment is healthy, a judgment that is subjective as the user is often pressured into accepting environments that objectively are not good for him or her. Stress management systems that focus only on measuring existing stress are too late, as the stress is already present, and cannot determine the cause of stress. hence these systems can only generate global feedback like "breathe deeply and slowly".

Figure 1:
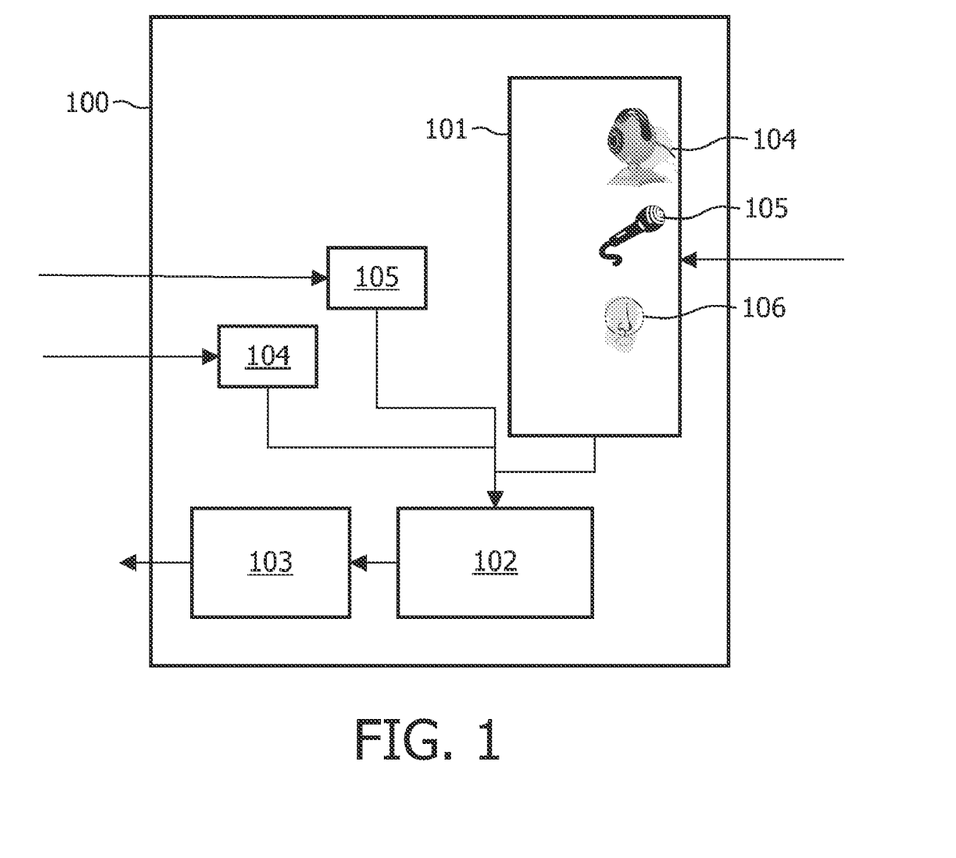
FIG. 1 shows a schematic diagram of an embodiment of the invention.

FIG. 1 shows a schematic diagram of a stressor detection system 100. The stressor detection system 100 comprises a sensor means 101 for obtaining a signal representing a physical phenomenon that the person is exposed to. The sensor means 101 may comprise, for example, a camera 104, a light sensor (not shown), a microphone 105, an electronic nose (e-nose) 106, a vibration sensor (not shown), or an accelerometer, advantageously a tri-axial accelerometer (not shown). The signals produced by the sensors are communicated to processing means 102. The processing typically involves a signal-processing step, such as determining the complexity of the signal or performing a time-frequency analysis. More complex signals are believed to be relatively stress inducing. The signal analysis results in a stressor value. The stressor value is communicated to the output means 103, which communicates the stressor value to a system coupled to the stressor detection system. This can for example be a PDA or a personal computer that uses the stressor value to provide an advice to the user. The output means 103 can store results and raw measurement data for later transfer to the system coupled to the stressor detection system. Also the output means 103 can provide feedback related to the stressor level using any suitable rendering device such as a display or a loudspeaker.

The sensory stressor sensor 100 measures the environmental signals that can be picked up by the senses of the user, and calculates a measure of physical/physiological burden on the user.

An alternative embodiment is a (mobile) phone, where the user calls a stressor-sensor-service phone number, which is answered by a stressor-sensor-server. The sound signals obtained from the microphone of the phone are transmitted to the server on the other end of the phone connection, and the processing hardware is comprised in the server, which sends and an SMS and/or voice message with results back to the phone and/or stores the stressor related information in a repository. Such a service phone number can also be used for a music recognition service. Signals obtained from other sensors integrated in and/or connected to the (mobile) phone, for example a camera or an accelerometer, may also be transmitted to the stressor-sensor-server. The signals may be pre-processed before transmitting to the stressor-sensor-server. Similarly, any client/server configuration such as a client personal computer with peripherals or a personal digital assistant comprising sensor means (for example microphone, web cam) communicating with a server comprising processing means can also be realized.

The signal processing provided by processing means 102 preferably comprises establishing a complexity of the signal. The complexity may be established by computing the amount of information in the signal or the entropy. Also a bound on a Kolmogorov complexity may be established. Such a bound is related to the compression ratio achieved by a suitable compression algorithm, the compression ratio relating to the size of the compressed signal expressed in a number of bits divided by the size of the (possibly pre-processed) raw signal obtained from the sensor means 101. In an embodiment, the algorithm for determining the stressor value comprises the following steps:

- determine the size in bits of the time-varying signal s representing a physical quantity relating to an environment of the person; denote this size as size(s);
- compress s to obtain a compressed signal $s_c$;
- determine the size in bits of the compressed signal $s_c$; denote this size as size ($s_c$);
- determine the compression ratio r by computing $r=size(s_c)/size(s)$.
- set the stressor value v equal to the compression ratio: $v=r$.

This way, if the stressor value v is close to 0, the signal is highly predictable (corresponding to absence of stressors) and if v is close to 1, the signal is highly unpredictable (corresponding to presence a stressor). Note that for example in music signals, a compression algorithm can compress a noise component with an especially low compression ratio if the decompressor comprises a corresponding noise generator. The human ear will not notice the difference between the original noise component and the noise component obtained from the noise generator. This is an example of a sense-specific compression algorithm, in that it compresses the signal to the maximal extend possible under the constraint that the original signal and the signal obtained by successively compressing and decompressing the signal, when rendered, cannot be distinguished by the person either consciously or unconsciously. Preferably before applying the algorithm above, any signal components that, when rendered, cannot be perceived by the person either consciously or unconsciously, are removed from the signal s. This results in an especially relevant compression ratio r and an especially accurate stressor value v.

An embodiment of the invention comprises a microphone 105, sound processing hardware and software 102, a display coupled to the output means 103, and interactive buttons. These components together form an apparatus that can be worn on the body.

In this embodiment of the invention, sound is measured. The sound pressure level and the changes in sound pressure level (envelope) plus dose (integral, moving average) influence the stress of users. Weights for sound level, sound envelope, and sound dose determine to what extend these measured quantities contribute to the stressor level. In an embodiment only absolute levels are measured, in a more advanced embodiment types of sounds are recognized and given individual weights. For example, certain sounds trigger instinctive alarms, for example crying babies; speech requires more cognitive effort than a repetitive tone; sound is directional and a movement of the origin of the sound requires more cognitive effort; changes in sound-sources are potentially stress inducing. When measured, these can all contribute to the stressor level.

Advantageously, the processing means 102 is arranged for establishing the loudness of the sound. The loudness is a psychoacoustic measure representing how loud a person experiences a sound signal. The loudness is related to the annoyance and stress caused by the sound signal. Annoyance is a known concept from acoustics, strongly related to the stressor value. See: "Handbook of acoustical measurements and noise control", C. M. Harris, $3^{rd}$ Edition, Acoustical Society of America, pages 23.1-23.7. The loudness of the sound can be found for example using a standardized method such as ISO532A or ISO532B. The loudness and/or annoyance can be used as a stressor value. A combination of both, such as a weighted sum, is also possible. Preferably the stressor value is determined also in dependence on a time at which the loudness and/or annoyance occurs, for example at night the stressor value may be higher than during the day, see also: "Fundamentals of acoustics", L. E. Kinsler et al., $3^{rd}$ Edition, John Wiley and Sons, New York, pages 284-291.

Another embodiment is formed by an apparatus comprising a light sensor or camera 104 and light or image processing hardware and software 102, an optional display coupled to output means 103 and optional interaction means that can be worn as a small device on the body. It can also comprise a microphone 105 and sound processing hardware and software 102 as described above. Sunlight and full spectrum light are good for lowering stress levels, but unnatural light, such as fluorescent light, in any intensity works as a stressor. A value relating to a light spectrum can be obtained from a spectral measurement system. An example of such a system is GS-1253-LCD from Gamma Scientific, San Diego, Calif., USA.

One of the outputs of such as system is a color-rendering index (CRI). The CRI is a measure of the ability of a light source to reproduce the colors of various objects being lit by the source. The best possible rendition of colors is specified by a CRI of one hundred, while the very poorest rendition is specified by a CRI of zero. For a source like a low-pressure sodium vapor lamp, which is monochromatic, the CRI is nearly zero, but for a source like an incandescent light bulb, which emits essentially blackbody radiation, it is nearly a hundred. The CRI is measured by comparing the color rendering of the test source to that of a "perfect" source, which is generally a black body radiator, except for sources with color temperatures above 5000K, in which case a simulated daylight is used. For example, a standard "cool white" fluorescent lamp will have a CRI near 62. It is believed that a low CRI is associated with stress. Another output of a spectral measurement system believed to be associated with stress is a color temperature (CT).

Rather than measuring a steady spectrum of light, the spectral measurement system for use with the stressor detection system preferably operates in a continuous mode. That way, the CRI and/or color temperature (CT) or other relating quantities are known continuously. Usually a spectral measurement system measures the spectrum of a single light source. For use with the stressor detection system, it is preferred that the spectral measurement system measures the CRI, color temperature, or other relating quantities of (non-directional) environmental light. By measuring CRI or CT or other relating quantity of environmental light continuously, a signal is obtained representing the respective quantity. By providing to the processing means 102 the time of day, the signal can be associated with the times at which measurements were made. Preferably, a reference signal representing the respective quantity as a function of the time of day is made available to the processing means 102. The reference signal corresponds to the respective quantity under ideal circumstances. Alternatively, the reference signal corresponds to the respective quantity under for example normal, average, or undesirable circumstances. Preferably, one or more such signals associated with known stressor values are made available to the processing means 102. By comparing the measured signal with one or more reference signals, a comparison between the current environment of a person and the reference signals can be made. From such a comparison, the stressor value can be obtained. For example, if the currently measured signal, taken into account the time of day, compares for 80% to a reference signal associated with a stressor value of 0.2 and it compares for 20% to a reference signal associated with a stressor value of 0.7, the processing means could determine a stressor value of 0.3. Similarly, the seasonal influences may be incorporated by providing to the processing means 102 the time of year and reference signals corresponding to different times of year.

Changes in light intensity contribute to the stressor level. Epilepsy can be induced by stroboscope light. A weight determines to what extend the light envelope contributes to the stressor level. In another embodiment, light is not treated as a uniform source, but as its individual color components or even as an image. The inherent complexity of the image can be determined using for example edge detection, counting individual areas. The amount of movement over time can be calculated using known motion estimation techniques. The image complexity and the amount of movement over time add to the stressor level with predetermined respective weights, as it requires more cognitive effort by the brain to process these images. In another embodiment, objects can be recognized, and weights can be attributed to types of objects. For example, weapons can be associated with a positive weight, and flowers can be associated with a negative weight.

Another embodiment comprises a Tracmor activity meter that can measure accelerations of the human body, when worn on the body, by focusing on certain frequency-ranges that the human body operates in, and can filter out most externally induced accelerations. Human motion typically occurs in a certain frequency range, and the lower frequencies and higher frequencies are externally induced. In traditional activity meters, the frequency components of accelerations generated by a person are used for determining an energy expenditure of the person. See: "Quantitating physical activity in COPD using a triaxial accelerometer", by B. G. Steele et al., CHEST, May 2000. For example frequencies above 16 Hz are associated with vehicular transportation rather than physical activity. In the stressor detection system according to the invention, the other acceleration signal components are used, namely the accelerations induced by forces external to the person, because these forces may cause stress or relaxation of the person. Using the externally induced accelerations as a basis, a stressor sensor for vibration and acceleration is obtained. The activity meter and stressor sensor can optionally be integrated in the same device, although optimal placement of the device might lead to two devices, for example one on the belt and one on the neck. A wired or wireless connection can be used to couple the two devices. Advantageously, the stressor detection system 100 further comprises an electromyography system 104 for obtaining a value related to a muscle contraction. The processing means is arranged for associating accelerations shortly after a muscle contraction as a movement pattern induced by the person himself, and for associating other accelerations with externally induced movements or forces. Users can be stressed from externally induced movements, like vibrating/accelerating areas such as trains or automobiles. A difference between high-frequency accelerations (typically vibrations and shocks) and low-frequency accelerations can be made, with different weights. In particular, unpredictable forces and movements are stressors. An example of a situation with such unpredictable forces is a moving train or bus. The unpredictable forces are caused by the roughness of the rails or roads. An example of a relaxing or stress-reducing movements is a soft rocking. Such a movement is particularly predictable.

Another embodiment comprises an electronic nose (e-nose) 106 and/or an odor sensor. Preferably an e-nose operating at room temperature is used when the stressor sensor is worn on the body. The embodiment further comprises e-nose signal processing hardware and/or software 102. The e-nose can establish the concentration level of at least one volatile organic compound. See: "An improved integrated electronic nose for online measurement of VOCs in indoor air", by F. Xiangsheng et al., Proc. IEEE Engineering in Medicine and Biology $27^{th}$ Annual Conference, Shanghai, China, 2005. Preferably the e-nose is arranged for establishing concentration levels of volatile organic compounds that are known to be irritating or stress inducing in a person. The stressor value can be a weighted sum of concentration levels of volatile organic compounds, wherein relatively stress-inducing compounds are associated with a relatively high weight. Preferably, the processing means 102 is arranged for detecting changes in the time-varying concentration levels. A smell often becomes less stress inducing when the smell remains relatively the same for a longer period of time. An increase of the concentration of a volatile organic compound that is perceived by the person as a particularly bad smell results in a relatively large stressor value. If the concentration remains constant, the stressor value gradually decreases because the corresponding bad smell is perceived with a gradually decreasing intensity. For example, a person entering a livestock building may experience stress caused by an overwhelming smell, whereas the person after having worked inside for a couple of hours hardly notices the smell any more and consequently no longer experiences the high concentration of the involved volatile organic compound as a stressor. E-noses known in the art comprise a significant amount of signal processing for establishing the concentration of a volatile organic compound. Preferably the signal processing of the e-nose and the signal processing for establishing the stressor value are performed using the same processor and/or memory component.

As a direct feedback to the user, the output means 103 of the stressor sensor in any of the previously described embodiments presents a measure of how stressful the environment is, and summarizes this over a period of time. For example, the situation of the last minute or few seconds can be reported on. This might prompt a user to leave an area that violates stress-relating criteria, for example labor law criteria.

Also, the period from the time of waking up may be used. This might help a user better understand his own physiology, as he becomes aware of what external factors impinge on his senses. The total sleeping time can be included in the equation, as insufficient sleep means that a certain level of stress of the previous day carries over into the next day. In this case, the stressor level is not totally reset to zero at wakeup time, but starts at a fraction of the previous day, that fraction can be related to the duration and quality of sleep. Optionally, the stressor sensor could show a comparison with stressor sensors of other users, such as peer groups or friends. this could help a user to decide whether the current level is acceptable. The stressor sensor can show trends and history data, allowing a user to see if the situation is improving or not.

The stressor sensor can show what external signals most contributed to the current stressor level, and can show individual levels of sound, light/images, and acceleration. This gives the user precise feedback on what environmental circumstances have to be changed. The stressor sensor may suggest methods of lowering the level of stressors like lower light intensity, protective eyewear or ear wear.

To extend the stressor sensor to include aspects of symbolic stressors, a link to a digital agenda and/or project planning software can be made, as a large number of different tasks and deadlines are also stress inducing. Also, a link to a work pace program may be made, as work pace programs typically check user computer activity, which can have a weight as well. A global positioning system can be given a stressor weight as well, as traveling gives many new experiences that require cognitive effort and stress may be associated with a specific location. The stressor sensor can be linked to an in-car stress management system, such that driving-related symbolic stressors can be taken into account effectively.

In an embodiment, the stressor detection system 100 further comprises stress detection means 105 for obtaining a stress value relating to stress experienced by the person. This value is passed to the processing means. Herein, a relation between the stress value and the stress experienced by the person is established and improved. The stress detection means 105 comprises a stress sensor (for example, the stress detection means 105 comprises establishing pulse rate, body temperature, galvanic skin reflex (GSR), and/or voice pitch). Alternatively, the stress detection means 105 comprises a user interface for enabling the person to indicate to the stressor detection system information associated with the stress he experiences, and advantageously associated with the source or sources of stress. A combination of stress sensor and user interface can be used to advantage. The processing means 102 takes input from the stressor sensor(s) 101, the stress detection means 105, and/or the electromyography system 104, and learns over time how well a user can handle stressful environments and circumstances, using known pattern recognition/artificial learning techniques, for example based on weights assigned and by changing weights assigned. Said weights comprise parameters appearing in a model of the relation between the mentioned inputs and the stressor value. Once this is known, a user can be warned using the output means 103 when entering environments that lead (over time) to unhealthy levels of stress. Also, for example, a job description might say, "looking for stress-resistant person". This invention can quantify this requirement by comparing the changed weights to predetermined weights known to correspond to the desired properties of a stress-resistant person.

A different example is persons that need a certain level of excitement to feel well; this system can also quantify a lack of experiences and suggest a user to seek more. The system allows a user to interact with the system through a user interface, for example manually indicating how the user experienced a certain episode, giving suggestions, allowing a user to manually indicate symbolic stressors that subsequently can be recognized, fore example using image recognition software/agenda analysis software.

Figure 2:
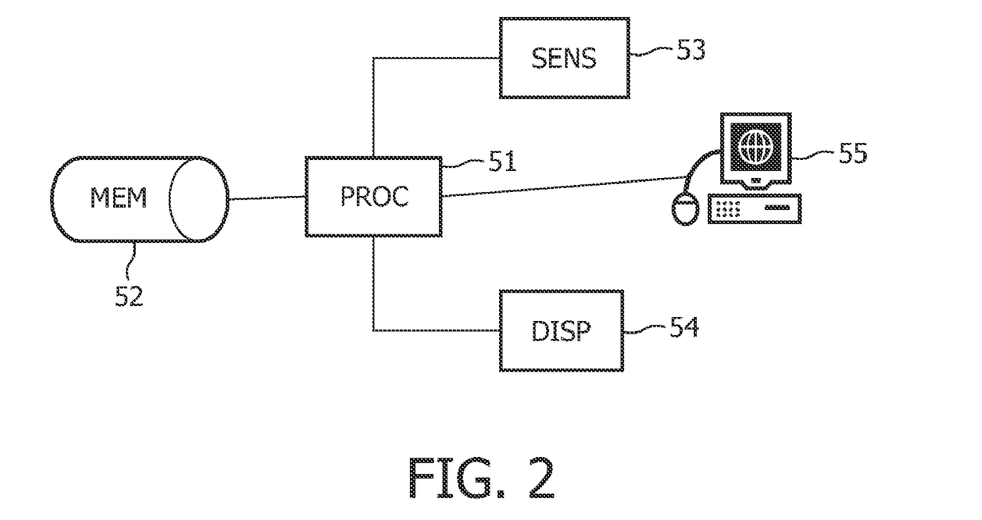
FIG. 2 shows another view of an embodiment of the invention.

FIG. 2 shows a sensor means 53 for being attached to a person for obtaining a time-varying signal representing a physical quantity relating to an environment of the person. The Figure also shows a processor 51 and memory 52. The processor 51 is connected to the sensor means 53 by means of a wired or wireless communication link, such as a USB interface, an analog cable with analog to digital conversion means, or a WLAN connection. The processor and memory are arranged for deriving a stressor value from the obtained signal. The processor and memory are also arranged for composing an output in dependence on the derived stressor value to be displayed on a display 54 for providing output related to the stressor value. The processor and memory are also arranged for transmitting the derived stressor value and/or a composed output to a personal computer 55 or to a server for further processing and reporting of the measured and processed signals. The memory contains instructions for being executed by the processor for providing the mentioned functionality. The personal computer or server can be connected to the processor 51 by means of a wired or wireless communication link, such as a USB interface or a WLAN connection.

A typical embodiment comprises software running on one of the involved devices or a remote server, and (wireless) connections between the involved devices, including a database and/or web connection.

The system can be used by users to get insight in the healthiness of the environments they are in and manage their stress levels more accurately. A simple version of the stressor sensor is realizable with existing low-cost technology. It can also be used to check the healthiness of a location by leaving the device in an environment on a dummy.

It will be appreciated that the invention also extends to computer programs, particularly computer programs on or in a carrier, adapted for putting the invention into practice. The program may be in the form of source code, object code, a code intermediate source and object code such as partially compiled form, or in any other form suitable for use in the implementation of the method according to the invention. The carrier may be any entity or device capable of carrying the program. For example, the carrier may include a storage medium, such as a ROM, for example a CD ROM or a semiconductor ROM, or a magnetic recording medium, for example a floppy disc or hard disk. Further the carrier may be a transmissible carrier such as an electrical or optical signal, which may be conveyed via electrical or optical cable or by radio or other means. When the program is embodied in such a signal, the carrier may be constituted by such cable or other device or means. Alternatively, the carrier may be an integrated circuit in which the program is embedded, the integrated circuit being adapted for performing, or for use in the performance of, the relevant method.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention claimed is:

1. A stressor detection system comprising:
a sensor adapted to be attached to a person for obtaining a time-varying signal representing a first physical quantity relating to an environment of the person, and
a processor which receives the time-varying signal from the sensor, compresses the time-varying signal to obtain a compressed signal, derives an amount of complexity included in the received signal by comparing the received signal and the compressed signal, and derives a first stressor value from the amount of complexity representing a degree to which the environment is inducing stress in the person, wherein signals with larger amounts of complexity derive a higher stressor value;
an output which provides feedback related to the stressor value.

2. The stressor detection system according to claim 1, wherein the processor performs a spectral frequency analysis of the received signal and derives a stressor value based on the spectral frequency analysis.

3. The stressor detection system according to claim 1, wherein the sensor obtains a second time-varying signal representing a second physical quantity relating to the environment of the person, the second physical quantity being different from the first physical quantity, and
the processor receives the second time-varying signal and derives a second stressor value from the second received signal and derives a combined stressor value from the first stressor value and the second stressor value.

4. The stressor detecting system according to claim 1, wherein the sensor includes a microphone and the time-varying signal includes an audible signal obtained from the microphone, and wherein the processor assigns a larger weight to a disturbing component of the audible signal, the disturbing component including at least one of:
frequencies above a predetermined bound and below an upper bound of frequencies that the person is able to hear, wherein the predetermined bound is smaller than the upper bound, and
frequencies below a predetermined bound and above a lower bound of frequencies that the person is able to hear, wherein the lower bound is smaller than the predetermined bound.

5. The stressor detection system according to claim 1, wherein the sensor includes a light sensor for obtaining a light intensity signal representing an intensity of visible environmental light and
the processor derives the stressor value based on the light intensity.

6. The stressor detection system according to claim 1, wherein the sensor includes a light sensor for obtaining a plurality of light signals each representing the intensity of a distinct color component of environmental light and
the processor derives the stressor value based on the light signals.

7. The stressor detection system according to claim 1, wherein the sensor includes a camera for obtaining at least one image and
the processor derives an amount of complexity of the at least one image and derives the stressor value based on the complexity of the at least one image.

8. The stressor detection system according to claim 7, wherein the processor derives an amount of movement from the at least one image and derives the stressor value based on the amount of movement.

9. The stressor detection system according to claim 7, wherein the processor performs an object recognition on the at least one image and derives the stressor value based on the object recognition.

10. The stressor detection system according to claim 1,
wherein the sensor includes an acceleration sensor for obtaining an acceleration signal, and
the processor extracts, from the acceleration signal, an externally-induced acceleration signal representing an acceleration of the person not caused by a muscle contraction of the person and derives the stressor value based on the externally-induced acceleration signal.

11. The stressor detection system according to claim 1, further including an electromyography system for obtaining an electromyography signal and wherein the processor derives the stressor value based on the electromyography signal.

12. The stressor detection system according to claim 1, further including a user interface enabling a person to indicate a stress value relating to stress experienced by the person, and wherein the processor establishes a relation between the stressor value and the stress experienced by the person.

13. The stressor detection system according to claim 1, wherein the processor determines a size of the time-varying signal, compresses the time-varying signal to obtain a compressed signal, determines a size of the compress signal, determines a compression ratio by comparing the size of the time-varying signal and the size of the compress signal, and derives the stressor value from the compression ratio.

14. The stressor detection system according to claim 1, wherein the sensor includes a microphone and the obtained time-varying signal includes an audio signal obtained from the microphone, and
the processor derives the stressor value based on at least one of:
an envelope of the audio signal,
a dose of the audio signal, and
a loudness of the signal.

15. A stressor detection method, the method comprising:
receiving a time-varying signal representing a physical quantity relating to an environment of a person from a sensor;
determining a size of the time-varying signal with a processor;
compressing the time-varying signal to obtain a compressed signal with the processor;
determining a size of the compress signal with the processor;
determining a compression ratio by comparing the size of the time-varying signal to the size of the compress signal with the processor;
deriving a stressor value from a time-varying signal with the processor, the stressor being based on the compression ratio;
outputting the stressor value.

16. The method according to claim 15, further including:
obtaining a second time-varying signal representing a second physical quantity with a second sensor, the second physical quantity being different from the physical quantity;
deriving a second stressor value from the second received signal; and
deriving a combined stressor value from the first stressor value and the second stressor value.

17. The method according to claim 15, wherein the sensor is at least one of an audio sensor, a light sensor, a camera, an odor sensor, an accelerometer and an electromyography sensor.

18. The method according to claim 15, further including:
indicating a stress value relating to stress experienced by the person through a user interface, and
establishing a relation between the stressor value and the stress experienced by the person.

19. The method according to claim 15, further including:
performing a spectral frequency analysis of the received time-varying signal; and
deriving a stressor value based on the spectral frequency analysis.

* * * * *